(12) United States Patent
Petit

(10) Patent No.: US 6,656,190 B2
(45) Date of Patent: Dec. 2, 2003

(54) IMPLANT PREHENSION DEVICE

(75) Inventor: Dominique Petit, Verton (FR)

(73) Assignee: Spinevision S. A. (FR)

( * ) Notice: Subject to any disclaimer, the term of this patent is extended or adjusted under 35 U.S.C. 154(b) by 67 days.

(21) Appl. No.: 09/804,660

(22) Filed: Mar. 13, 2001

(65) Prior Publication Data

US 2001/0025182 A1 Sep. 27, 2001

(30) Foreign Application Priority Data

Mar. 15, 2000 (FR) .............................................. 00 03390
Nov. 24, 2000 (FR) .............................................. 00 15226

(51) Int. Cl.⁷ .............................................. A61B 17/58
(52) U.S. Cl. .............................. 606/99; 606/86; 606/53
(58) Field of Search ............................. 606/60, 61, 99, 606/101, 104, 106

(56) References Cited

U.S. PATENT DOCUMENTS

| | | | | |
|---|---|---|---|---|
| 2,248,054 A | * | 7/1941 | Becker | 135/52 |
| 2,789,558 A | * | 4/1957 | Rush | 128/83 |
| 3,381,685 A | * | 5/1968 | Von Solbrig | 128/92 |
| 4,269,246 A | | 5/1981 | Larson et al. | |
| 5,176,709 A | * | 1/1993 | Branemark | 623/16 |
| 5,364,397 A | * | 11/1994 | Hayes et al. | 606/61 |
| 5,380,338 A | * | 1/1995 | Christian | 606/130 |
| 5,540,689 A | * | 7/1996 | Sanders et al. | 606/61 |
| 5,645,546 A | * | 7/1997 | Fard | 606/72 |
| 5,720,748 A | * | 2/1998 | Kuslich et al. | 606/80 |
| 5,720,751 A | * | 2/1998 | Jackson | 606/86 |
| 5,800,440 A | * | 9/1998 | Stead | 606/104 |
| 5,944,720 A | * | 8/1999 | Lipton | 606/61 |
| 5,957,927 A | * | 9/1999 | Magee et al. | 606/99 |
| 6,022,357 A | * | 2/2000 | Reu et al. | 606/99 |
| 6,139,549 A | * | 10/2000 | Keller | 606/61 |
| 6,402,759 B1 | * | 6/2002 | Strong et al. | 606/104 |
| 6,464,706 B1 | * | 10/2002 | Winters | 606/73 |
| 6,478,800 B1 | * | 11/2002 | Fraser et al. | 606/99 |

FOREIGN PATENT DOCUMENTS

| | | | | |
|---|---|---|---|---|
| DE | 0557 687 A1 | * | 1/1993 | ........... A61B/17/56 |
| EP | 0 442 629 A1 | | 8/1991 | |
| FR | 2 676 352 | | 11/1992 | |
| JP | 11070126 | | 3/1999 | |
| WO | WO 93/21848 A | | 11/1993 | |

* cited by examiner

*Primary Examiner*—Henry Bennett
*Assistant Examiner*—Nihir Patel
(74) *Attorney, Agent, or Firm*—Piper Rudnick LLP

(57) ABSTRACT

A prehension device for grasping an implant, implanting the implant and manipulating the implant including prehension means intended to cooperate with receiving means, wherein the prehension means has a form shaped like an arc of a circle, the peripheral edges of which are provided with at least one peripheral chamfer. The invention also pertains to a surgical instrument equipped with a prehension device and to an implant equipped with a prehension device.

9 Claims, 3 Drawing Sheets

FIG. 1
FIG. 2
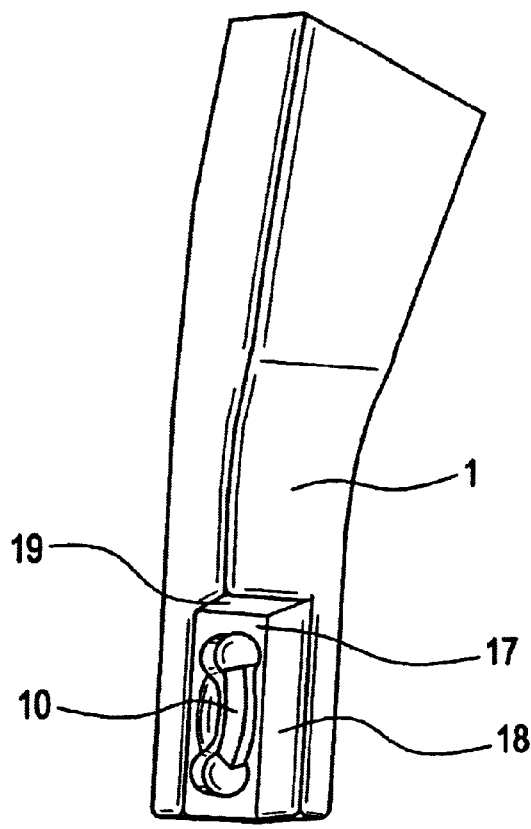
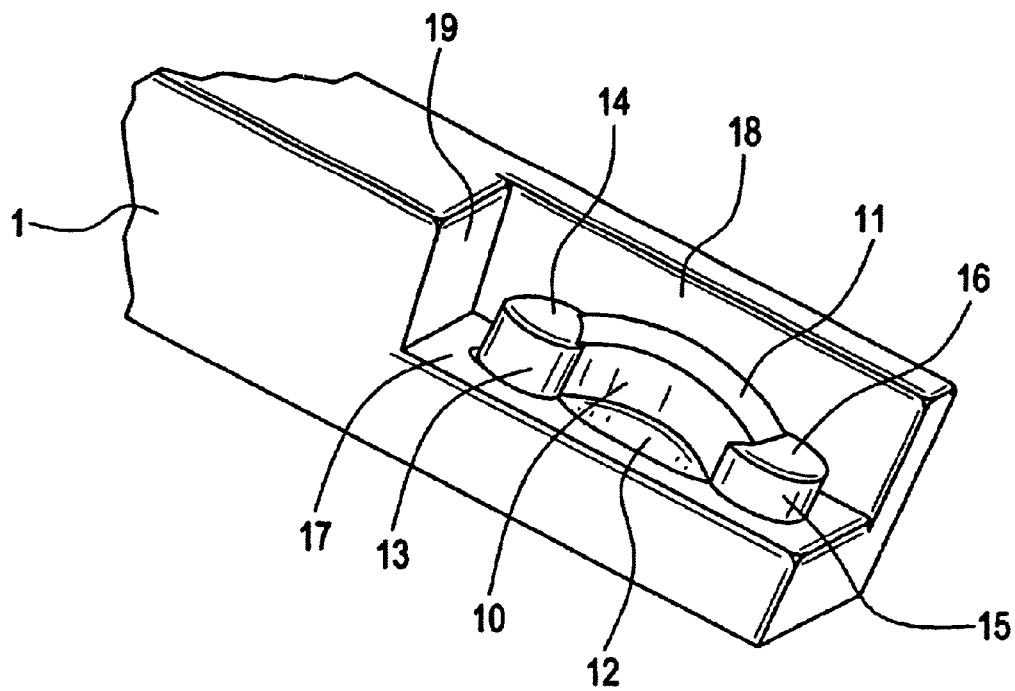

IMPLANT PREHENSION DEVICE

FIELD OF THE INVENTION

This invention pertains to a device making it possible to grasp an implant, implant the implant and manipulate the implant, of the type comprising prehension means intended to cooperate with receiving means. The field of application is that of spinal osteosynthesis devices.

BACKGROUND

Spinal osteosynthesis devices are traditionally arranged on the vertebral column by means of implants that are fixed, for example, in the pedicles. Thus, these implants can be, for example, pedicle screws. Grasping these implants by specific instruments is required for their installation on the spine.

It is not always easy to grasp the implant with the specific instrument because of the position of the implants (sometimes almost horizontal), because of the mobility of the implants (principally for hooks) and because of the constraints of congestion in the wound (surrounding tissues, depth of the wound, bony parts, etc.). In addition, installation of a spinal osteosynthesis device requires implementation of correction operations on the implants. During these correction operations, it is also necessary to hold these implants firmly either for introducing the connecting element (rod), or for installation or for maintaining the implants in their optimum positions.

In order to do this, one uses surgical instruments comprising particular prehension devices capable of cooperating with receiving means provided, for example, on said implant. Three types of implant prehension systems are presently available:

First type: A cylinder is provided on the instrument and this cylinder can cooperate with a hole provided on the implant. The prehension device furthermore has a stop which, when it comes into contact with a slot provided at the periphery of the hole or on the top of the implant, makes possible holding and rotational locking. This solution is acceptable, rather easy to install, but requires a large surface area on the implant for the prehension holes.

Second type: The invention has two pins which can cooperate with two holes provided on the implant. This attachment system requires perfect alignment of the implant and the instrument, and makes in-situ prehension very difficult.

Third type: An oblong hole is provided on the implant and the instrument has a projection of corresponding shape. This system also requires perfect alignment and makes anchoring very difficult.

SUMMARY OF THE INVENTION

This invention relates to a prehension device for grasping an implant, implanting the implant and manipulating the implant, including prehension means cooperative with receiving means, wherein prehension means has in longitudinal section an arc-shaped form, the peripheral edges of which are provided with at lest one peripheral chamfer and the arc-shaped form has at one end at least one cylinder.

BRIEF DESCRIPTION OF THE DRAWINGS

Better comprehension of the invention will be provided by the description below, presented purely for explanatory purposes, of one mode of implementation of the invention with reference to the attached figures:

FIG. 1 shows a partial perspective view of the prehension means of a prehension device according to the invention, FIG. 2 shows a detail view, from another perspective, of the prehension device of FIG. 1.

DETAILED DESCRIPTION

The present invention resolves the disadvantages of the prior art by providing a prehension device comprising prehension means that create with the receiving means a prehension interface that is easy and quick to implement and effective. To do this, the invention is of the type wherein the prehension means present in longitudinal section a form shaped essentially like an arc of a circle the peripheral edges of which are provided with at least one peripheral chamfer.

In a preferred version of the invention the arc-shaped form furthermore presents at its base at least one base chamfer and at one end at least one cylinder with a substantially conical or substantially spherical end, and the prehension means have a prepositioning stop with at least two surfaces. In this preferred version of the invention, the receiving means has a form that is complementary to that of the prehension means. The receiving means and the prehension means can be indifferently of recessed or relief form and positioned on the surgical prehension instrument or on the implant.

Thus, during the use of the prehension interface, the prehension means and the receiving means automatically are substantially centered in relation to each other, sliding on the chamfers and creating a solid and precise grip. Advantageously, the device according to the invention makes it possible to position receiving means at different sites on the implant. Advantageously, the device according to the invention makes it possible to perform very precise prehension operations on the implants even when they are difficult to access.

The present invention also pertains to a surgical instrument equipped with at least one prehension device according to the invention and to an implant equipped with at least one prehension device according to the invention.

Figure 3:
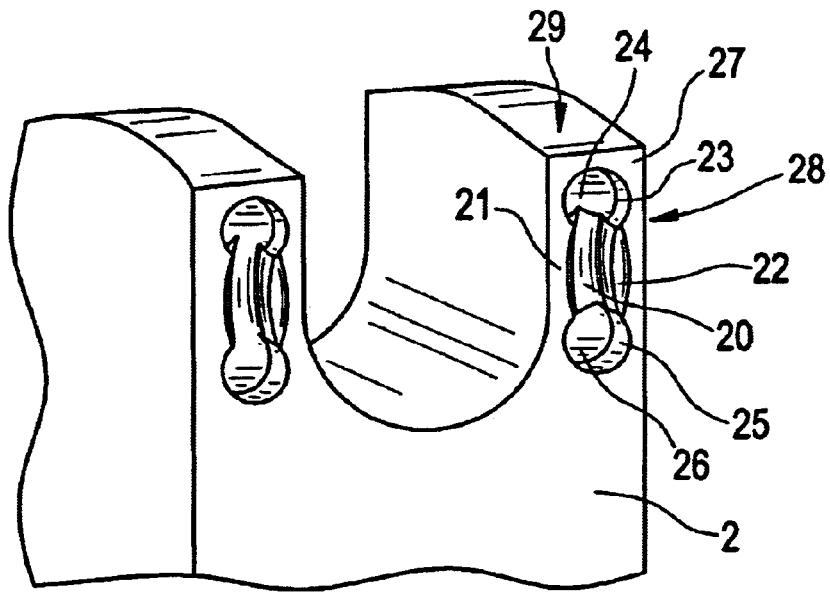
FIG. 3 shows a partial perspective view of the receiving means.

Turning now to the drawings, the device according to the invention is a prehension device (1) making it possible to grasp an implant (2), implant it and manipulate it, of the type comprising prehension means, shown in FIGS. 1 and 2, intended to cooperate with receiving means, shown in FIG. 3. In the illustrated mode of implementation of the invention, the prehension means are in relief and the receiving means are recessed, but the opposite can also be true. Furthermore, the prehension means are positioned on the surgical instrument and the receiving means are positioned on the implant, but the opposite can also be true.

The prehension device (1) according to the invention is characterized in that the prehension means has in longitudinal section a shape that is essentially an arc of a circle (10), the peripheral edges of which are provided with at least one peripheral chamfer (11). The arc-shaped form (10) is of the slender quarter-moon type and has a certain width on the order of from several tens of millimeters to several millimeters. Both of the two peripheral edges of the arc-shaped form (10) are preferably fitted with a peripheral chamfer (11). The shape of the receiving means of the implant (2) is also, in longitudinal section, essentially an arc of a circle (20) as shown in FIG. 3.

In the figures, the prehension means comprise a stop in relief form while the receiving means form a hole.

FIG. 3 shows an implant (2) comprising two sets of receiving means positioned on both sides of a U-shaped form. However, for reasons of clarity only one set of receiving means was referenced. In actuality, depending on the difficulties encountered during the correction operations, it can be preferable to use one set of receiving means or the other set.

This positive and negative quarter-moon form makes possible a simplified fitting of the instrument onto the implant (2). This form of prehension does not require perfect alignment of the instrument in relation to the implement during the correspondence operation, but the peripheral chamfers (11) of the instrument enable a subsequent substantially automatic alignment when the instrument is locked against the implant by cooperation with a receiving zone (21) provided at the bottom of the receiving means and having in cross section an essentially U shape, possibly with a beveled V-shaped bottom.

To enhance this automatic alignment effect, at least one chamfer (22) and preferably two chamfers (22) are provided on the side of the receiving means of the implant (2). In order to increase the mechanical resistance of the grip on the instrument, at least one base chamfer (12) and preferably two base chamfers (12) are provided at the base of the arc-shaped form (10) of the prehension device (1). Each base chamfer (12) corresponds to a chamfer (22) provided on the side of the receiving means of the implant (2), in a manner so as to not obstruct the complete locking of the instrument onto the implant (2).

So as to minimize the risk of pullout due to the traction of the instrument in relation to the implant (2), a cylinder (13) is provided on the socket of the prehension device (1), at one end of the arc-shaped form (10). A hole (23) capable of cooperating with the cylinder (13) is provided on the socket of the implant (2) at the corresponding end of the arc-shaped form (20). The height of this cylinder (13) must be smaller than the total height of the arc-shaped form (10) in a manner such that the arc-shaped form (10) implements the realignment of the prehension means in relation to the receiving means before the cylinder (13) comes into contact with the surface of the hole (23).

This cylinder (13) preferably has a conical end (14) so as to facilitate the cooperation between the prehension means and the receiving means. The hole (23) has a conical bottom (24) corresponding to the conical end (14) of the cylinder (13). The conical end (14) can be, for example, spherical. The conical bottom (24) is then also spherical.

In one preferred implementation, the prehension device (1) has at the other end of the arc-shaped form (10) a cylinder (15) which is essentially identical to the cylinder (13) to make it possible to increase the mechanical resistance to pullout due to traction. The height of the cylinder (15) must be smaller than the total height of the arc-shaped form (10). A hole (25) corresponding to the cylinder (15) is also provided on the socket of the implant (2) at the other end of the arc-shaped form (20) in relation to the hole (23). The cylinder (15) also has a conical end (16) and the hole (25) also has a conical bottom (26). The conical end (16) can be, for example, spherical. The conical bottom (26) would then also be spherical.

The axes of the cylinders (13, 15) are essentially parallel to the mean longitudinal plane of the arc-shaped form (10) and the axes of the holes (23, 25) are essentially parallel to the arc-shaped form (20). The conical end (14) as well as the conical end (16) can be replaced by chamfers.

The receiving means are preferably located on a receiving surface (17) and the prehension means are located on a principal prehension surface (27). The essential element of the contacts between the prehension means and the receiving means is thus implemented between the receiving surface (17) and the principal prehension surface (27).

Figure 5:
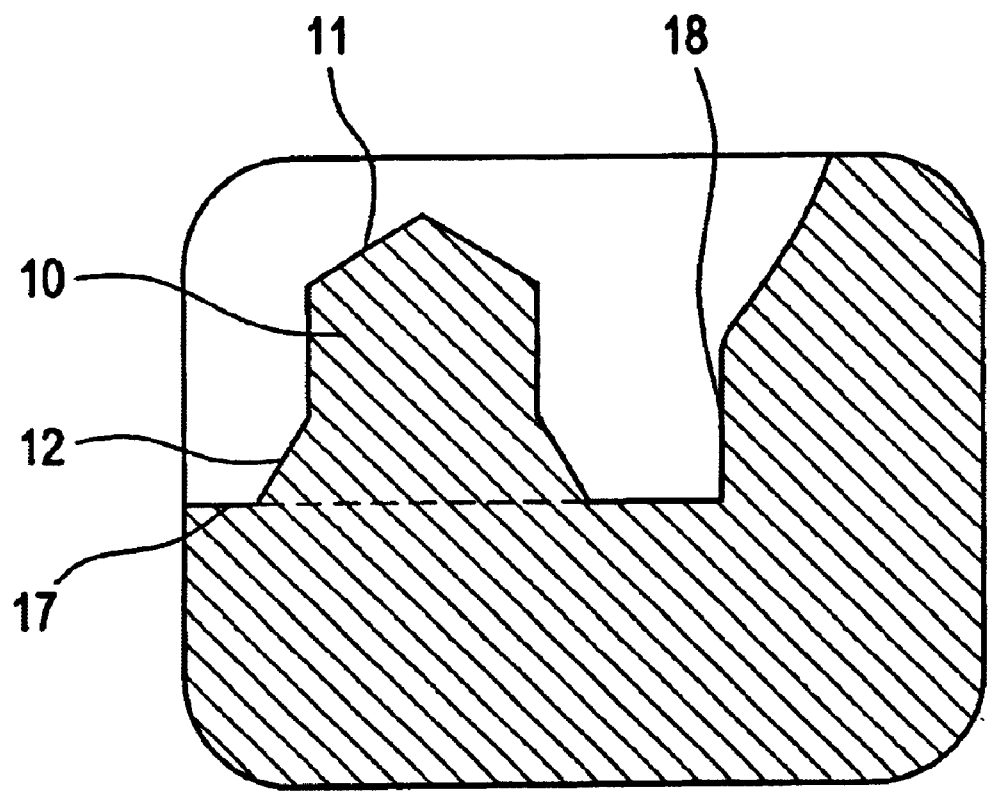
FIG. 5 shows a partial sectional view of the prehension means.

A prepositioning stop having at least two surfaces (18, 19), positioned essentially according to the end angle of the implant, can also be provided on the instrument to enable a prepositioning of the prehension device (1) above the principal prehension surface (27) of the implant (2). This prepositioning stop preferably has rounded sides as shown in FIG. 5. The surfaces (18, 19) of the prepositioning stop are intended to cooperate respectively with the angle surfaces (28, 29) of the principal prehension surface (27). The prepositioning stop preferably is of a height greater than the height of the arc-shaped form (10).

Figure 4:
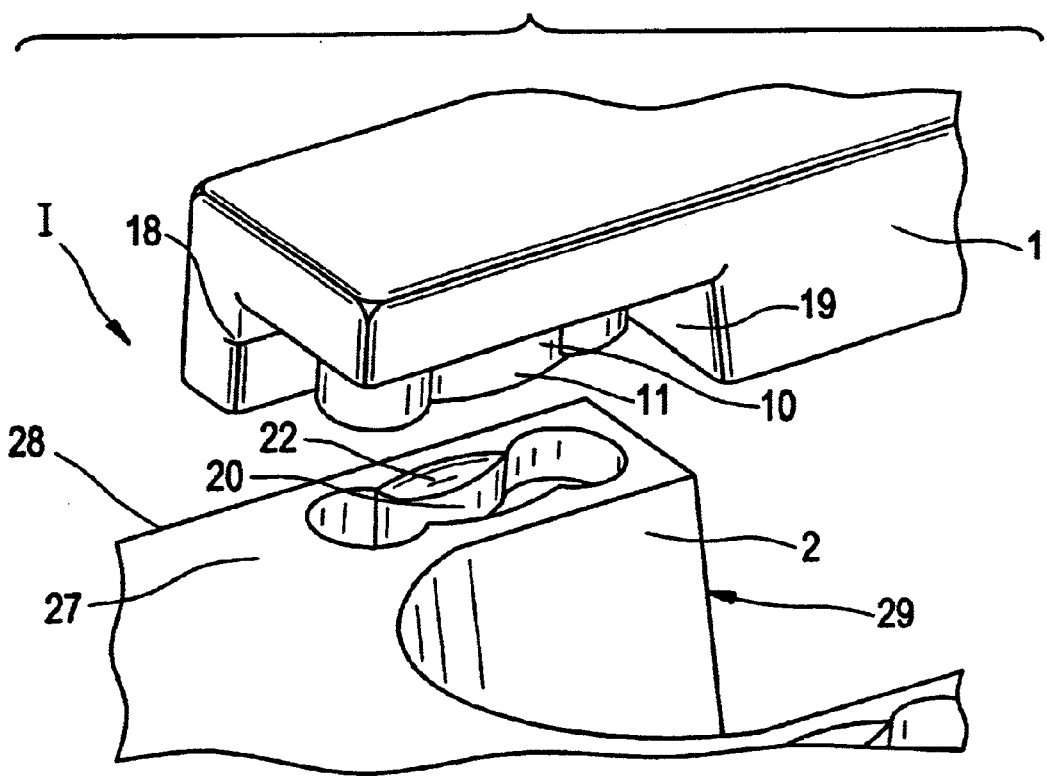
FIG. 4 shows an exploded perspective view of the interface between the prehension means and the receiving means.

The prehension interface I, in its most complete version, is thus defined as the cooperation, respectively, between the elements (10, 11, 12, 13, 14, 15, 16, 17) and (20, 21, 22, 23, 24, 25, 26, 27). FIG. 4 shows a view of this interface I.

What is claimed is:

1. A prehension device for grasping an implant, implanting the implant and manipulating the implant, comprising:
   prehension means cooperative with receiving means of the implant, wherein prehension means has in longitudinal section an arc-shaped form, the peripheral edges of which are provided with at least one peripheral chamfer and the arc-shaped form has at one end at least one cylinder.

2. The prehension device according to claim 1, wherein the arc-shaped form has a base and at least one base chamfer at the base.

3. The prehension device according to claim 1, wherein the cylinder has a substantially conical end.

4. The prehension device according to claim 3, wherein the conical end(s) is (are) substantially spherical.

5. The prehension device according to claim 1, wherein the prehension means has a prepositioning stop having at least two surfaces.

6. The prehension device according to claim 1, wherein the receiving means has a form which is cooperative with that of the prehension means.

7. The prehension device according to claim 1, wherein the height of the cylinder(s) is smaller than the total height of the arc-shaped form.

8. A surgical instrument comprising:
   at least one prehension device for grasping an implant, implanting the implant and manipulating the implant, comprising:
   prehension means cooperative with receiving means of the implant, wherein prehension means has in longitudinal section an arc-shaped form, the peripheral edges of which are provided with at least one peripheral chamfer and the arc-shaped form has at one end at least one cylinder.

9. An implant comprising:
   receiving means for cooperative use with at least one prehension device for grasping an implant, implanting the implant and manipulating the implant, comprising:

prehension means cooperative with receiving means of implant, wherein prehension means has in longitudinal section an arc-shaped form, the peripheral edges of which are provided with at least one peripheral chamfer and the arc-shaped form has at one end at least one cylinder.

* * * * *